(12) United States Patent
Ferrari

(10) Patent No.: US 8,093,917 B2
(45) Date of Patent: Jan. 10, 2012

(54) SAMPLING APPARATUS

(75) Inventor: Sarah Ferrari, Hagerstown, MD (US)

(73) Assignee: Evapco, Inc., Westminster, MD (US)

( * ) Notice: Subject to any disclaimer, the term of this patent is extended or adjusted under 35 U.S.C. 154(b) by 478 days.

(21) Appl. No.: 12/345,979

(22) Filed: Dec. 30, 2008

(65) Prior Publication Data

US 2010/0163127 A1    Jul. 1, 2010

(51) Int. Cl.
  *G01R 31/00* (2006.01)
  *G01N 33/20* (2006.01)
  *F16K 37/00* (2006.01)
(52) U.S. Cl. ............... 324/750.01; 73/861.01; 73/61.43; 137/625.28
(58) Field of Classification Search ........................ None
See application file for complete search history.

(56) References Cited

U.S. PATENT DOCUMENTS

| | | | | |
|---|---|---|---|---|
| 3,402,690 A | * | 9/1968 | Willis | 116/220 |
| 4,644,967 A | * | 2/1987 | Wyatt et al. | 137/599.05 |
| 7,114,336 B2 | * | 10/2006 | Hommema | 60/734 |

* cited by examiner

*Primary Examiner* — Vinh Nguyen
(74) *Attorney, Agent, or Firm* — Rader, Fishman & Grauer PLLC; Carl Schaukowitch

(57) ABSTRACT

A sampling apparatus for sampling a fluid from a fluid source includes a first fluid passage device, a second fluid passage device and a fluid by-pass. The first fluid passage device is disposed downstream of and in fluid communication with the fluid source. The second fluid passage device is disposed downstream of and is in fluid communication with the first fluid passage device. The fluid by-pass is disposed downstream of the fluid source and upstream of the second fluid passage device. The fluid by-pass being in fluid communication with and disposed between the fluid source and the second fluid passage device is operative to cause a first portion of the fluid to flow through the first fluid passage device and to cause a second portion of the fluid to by-pass the first fluid passage device and to flow to the second fluid passage device.

27 Claims, 7 Drawing Sheets

SAMPLING APPARATUS

FIELD OF THE INVENTION

The present invention relates to a sampling apparatus. More particularly, the present invention is directed to a sampling apparatus for use with evaporative cooling equipment such as fluid coolers, evaporative condensers and cooling towers.

BACKGROUND OF THE INVENTION

Evaporative cooling equipment dissipates heat by evaporation of the re-circulating cooling water. As the re-circulating cooling water evaporates, the concentration of any dissolved minerals in the re-circulating cooling water increases which can result in scaling and corrosion of the evaporative cooling equipment.

As is commonly known in the art, once the mineral buildup reaches a pre-determined threshold level, the mineral-laden re-circulating cooling water is then bled, commonly known as "blow-down", from the evaporative cooling equipment and replaced with make-up water that contains a lower concentration of minerals. Conductivity of the re-circulating cooling water is sometimes measured to reflect the mineral content thereof. When the mineral buildup reaches the threshold level thereby raising the conductivity to a threshold amount, a blow-down valve is activated in order to replace the mineral-laden re-circulating cooling water with make-up water to lower the concentration of the dissolved minerals in the re-circulating cooling water.

Blow-down of the evaporative cooling equipment occurs as follows: When the mineral content of the re-circulating cooling water, and hence the conductivity of the re-circulating cooling water, reaches a pre-determined threshold level, a controller reading the threshold amount of conductivity sends a signal to open the blow-down valve thereby directing the mineral-laden re-circulating cooling water to drain away from the evaporative cooling equipment. As the re-circulating cooling water volume drops, make-up water is automatically added thereto. Since the make-up water contains less minerals than the re-circulating cooling water, dilution of the concentration of the dissolved minerals in the re-circulating cooling water occurs thereby causing the conductivity of the re-circulating cooling water to be lowered below the threshold amount of conductivity. When the threshold amount of conductivity is achieved, the blow-down valve closes. Thus, the mineral concentration of the re-circulating cooling water remains within a predetermined range that is acceptable for operating the evaporative cooling equipment.

A prior art sampling and blow-down arrangement for evaporative cooling equipment is illustrated in FIG. 1. In a diagrammatical scheme, an evaporative cooling system 110 re-circulates cooling water through a cooling tower 112 via a pump 114 interconnecting an upstream conduit 116 as a source of the cooling water to the pump 114 from the cooling tower 112 and a downstream conduit 118 to pump the cooling water to the cooling tower 112. A sampling circuit 120 interconnects the upstream conduit 116 and the downstream conduit 118 so that a sample of the re-circulating cooling water can be diverted therethrough. The sampling circuit 120 includes an upstream shut-off valve 124 disposed adjacent to conduit 118, a downstream shut-off valve 122 disposed adjacent to conduit 116, a conductivity sensor 126 disposed between the upstream shut-off valve 122 and the downstream shut-off valve 124, a flow switch 128 disposed between the upstream shut-off valve 122 and the conductivity sensor 126 and a 'Y' strainer 130 disposed between the conductivity sensor 126 and the downstream shut-off valve 124. A bleed line 132 having a blow-down valve 134 is connected to the downstream conduit 118 and is disposed between a drain 135 and the downstream conduit 118. A make-up water source 136 is disposed upstream of the pump 114 by way of example only. A controller 138 reads the conductivity signal from the conductivity sensor 126 and the flow switch 128, then appropriately operates the blow-down valve 134. The make-up water source 136 operates off a float or other method to detect low water level. This combination of components will maintain a desired range of conductivity of the cooling water as is well known in the art.

Another prior art sampling and blow-down arrangement for evaporative cooling equipment is illustrated in FIG. 2. This prior art sampling and blow-down arrangement is similar to the one illustrated in FIG. 1 except where the bleed line 132 and associated blow-down valve 134 are located. In this diagrammatical scheme of FIG. 2, the bleed line 132 and the associated blow-down valve 134 are connected between the upstream shut-off valve 122 and the flow switch 128. Otherwise, this prior art sampling and blow-down arrangement operates as the one in FIG. 1.

Although each one of the prior art sampling and blow-down arrangements for evaporative cooling equipment is effective, there is a drawback, particularly in freezing, or potentially freezing, environments. The sampling circuit 120, the bleed line 132 and the blow-down valve 134 must be heated and insulated to prevent freezing.

SUMMARY OF THE INVENTION

A sampling apparatus for sampling a fluid from a fluid source includes a first fluid passage device, a second fluid passage device and a fluid by-pass. The first fluid passage device is disposed downstream of and in fluid communication with the fluid source. The second fluid passage device is disposed downstream of and in fluid communication with the first fluid passage device. The fluid by-pass is disposed downstream of the fluid source and upstream of the second fluid passage device. Also, the fluid by-pass is in fluid communication with and disposed between the fluid source and the second fluid passage device. Additionally, the fluid by-pass is operative to cause a first portion of the fluid from the fluid source to flow through the first fluid passage device and to cause a second portion of the fluid to by-pass the first fluid passage device so that the second portion of the fluid flows from the fluid source to the second fluid passage device without flowing through the first fluid passage device.

Advantages and benefits of the present invention will be better appreciated in view of the detailed description of the exemplary embodiment of the present invention and the versions thereof taken with reference to the accompanying drawings, in which:

DETAILED DESCRIPTION OF THE EXEMPLARY EMBODIMENT AND VERSIONS THEREOF

Figure 1:
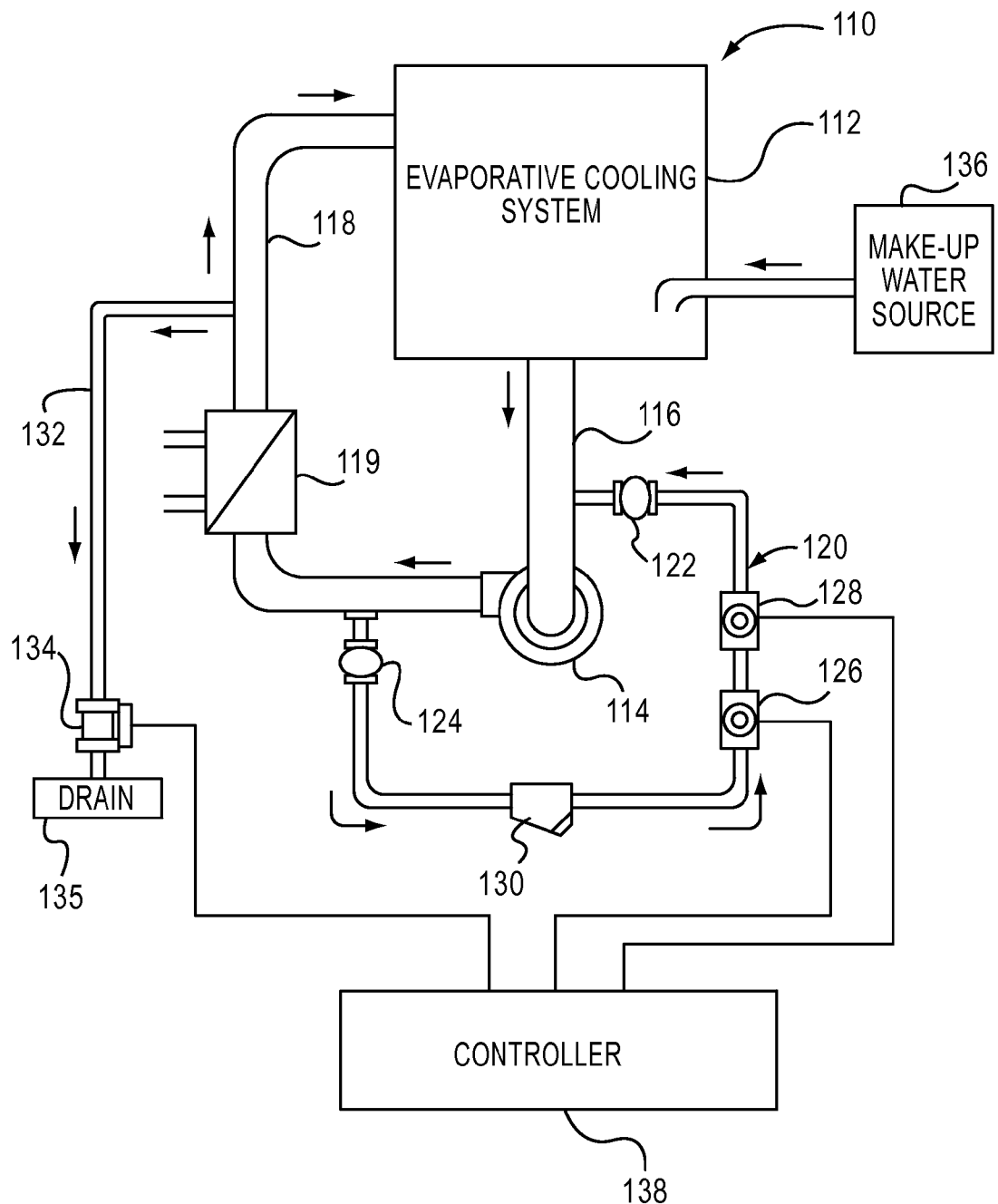
FIG. 1 is a diagrammatical view of a first prior art sampling apparatus operably connected to a conventional evaporative cooling system.
Figure 2:
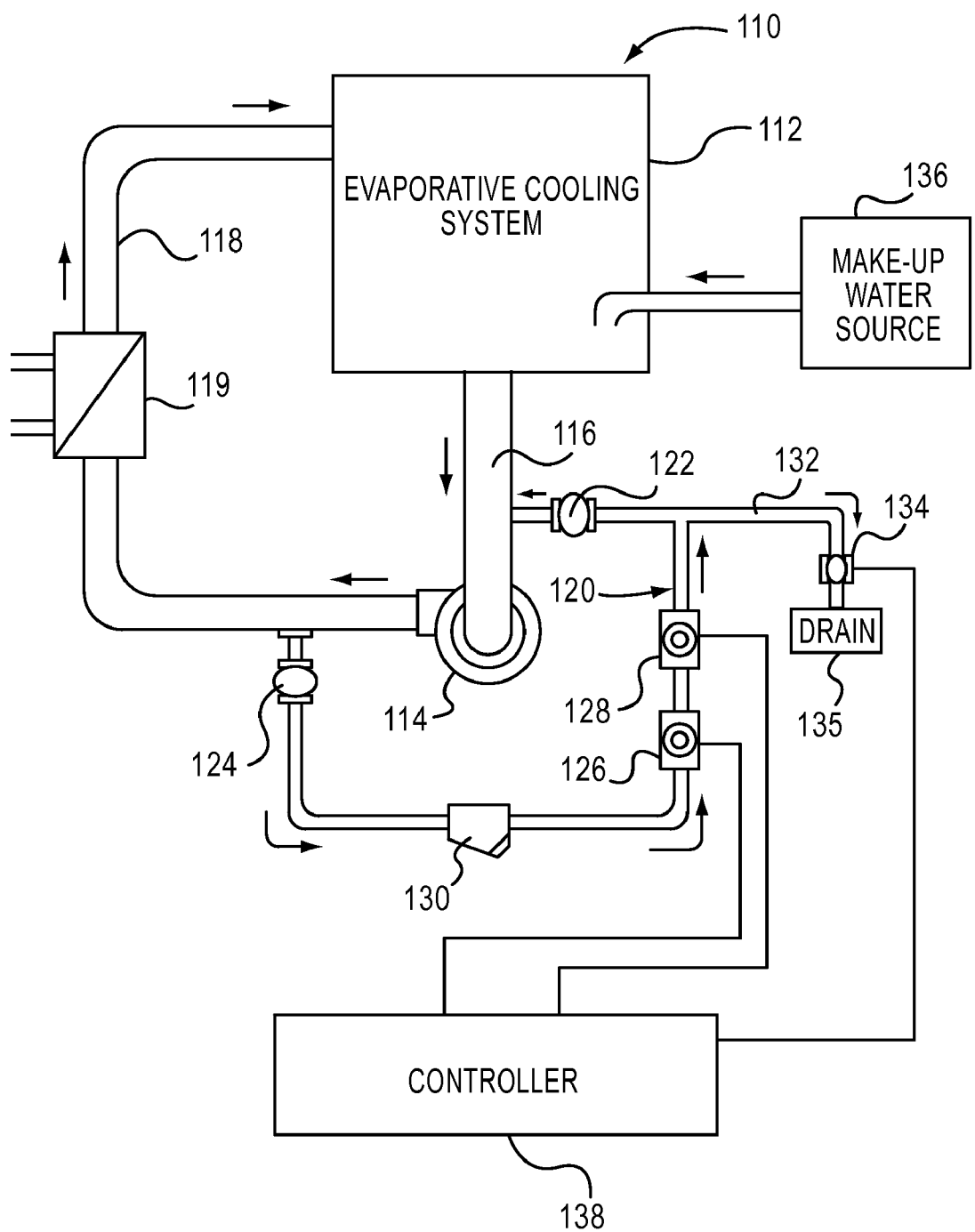
FIG. 2 is a diagrammatical view of a second prior art sampling apparatus operably connected to the conventional evaporative cooling system.

Hereinafter, embodiments of the present invention will be described with reference to the attached drawings. The structural components common to those of the prior art and the structural components common to respective embodiments of the present invention may be represented by the same symbols and repeated description thereof will be omitted.

An exemplary embodiment of a sampling apparatus 10 of the present invention is hereinafter described with reference to FIG. 3. Shown by way of example only and not by way of limitation, the sampling apparatus 10 of the present invention is employed with a conventional evaporative cooler 12. However, one of ordinary skill in the art would appreciate that the sampling apparatus 10 can be used for other applications. The evaporative cooler 12 has a water basin 14 containing cooling water CW, a cooling water distribution system 16 disposed above the water basin 14, a fan assembly 18 and a pump 20 for pumping the cooling water CW from the water basin 14 to the cooling water distribution system 16. The cooling water distribution system 16 is a spray system having a manifold 22 and a plurality of spray nozzles 24. As commonly known in the art, the conventional evaporative cooler 12 includes heat exchange coils 26 positioned between the spray nozzles 24 and the water basin 14 although it is known in the art that fill material (not shown) can be substituted for the heat exchange coils 26. Also, louvers 28 extend around a lower periphery of the evaporative cooler 12 to permit air represented by arrows labeled air adjacent the louvers 28 to enter in the evaporative cooler 12 and exit from the fan assembly 18 as illustrated by the arrow labeled air adjacent the fan assembly 18. Further, a riser pipe 30 interconnects the pump 20 with the manifold 22 so that the cooling water CW can be pumped from the water basin 14 to the manifold 22.

Figure 3:
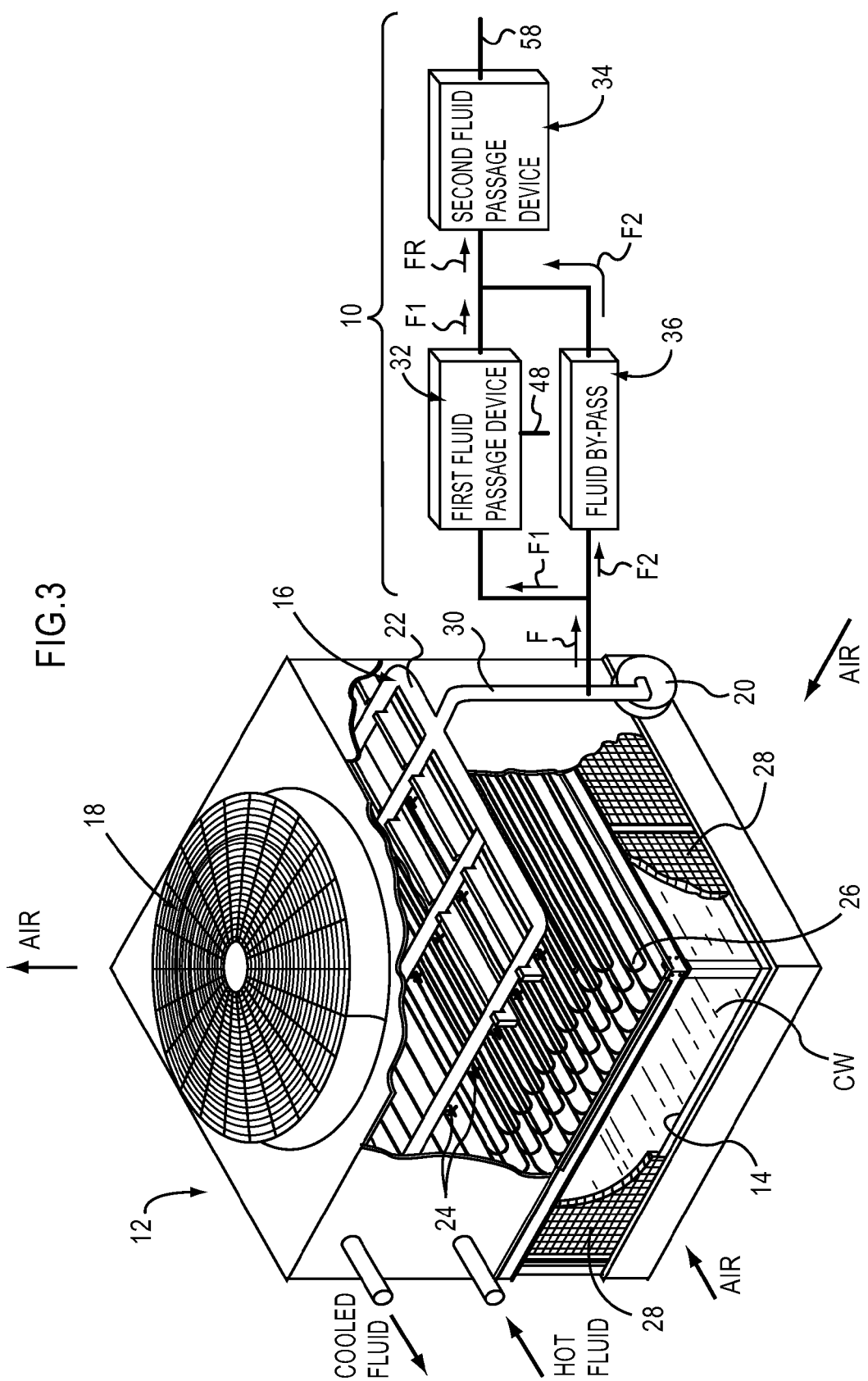
FIG. 3 is a diagrammatical view of a sampling apparatus of the present invention operably connected to a conventional evaporative fluid cooler.

In FIG. 3, the sampling apparatus 10 samples from a fluid represented by arrow F, in this case, the cooling water CW from a fluid source, in this case, the riser pipe 30, of the conventional evaporative cooler 12. The sampling apparatus 10 includes a first fluid passage device 32, a second fluid passage device 34 and a fluid by-pass 36. As illustrated in FIG. 3, the first fluid passage device 32 is disposed downstream of and is in fluid communication with the fluid source, i.e., the riser pipe 30. The second fluid passage device 34 is disposed downstream of and is in fluid communication with the first fluid passage device 32. The fluid by-pass 36 is disposed downstream of the fluid source, i.e., the riser pipe 30, and is disposed upstream of the second fluid passage device 34. The fluid by-pass 36 is in fluid communication with and is disposed between the fluid source, i.e., the riser pipe 30, and the second fluid passage device 34. Additionally, the fluid by-pass 36 is operative to cause a first portion represented by arrow F1 of the fluid F from the fluid source, i.e., the riser pipe 30, to flow through the first fluid passage device 32 and to cause a second portion F2 of the fluid F to by-pass the first fluid passage device 32 so that the second portion F2 of the fluid F flows from the fluid source, i.e., the riser pipe 30, to the second fluid passage device 34 without flowing through the first fluid passage device 32.

Again, with reference to FIG. 3, the first portion F1 of the fluid F and the second portion F2 of the fluid F rejoin each other, as represented by arrow FR, after the first portion F1 of the fluid F flows through the first fluid passage device 32 and the second portion F2 of the fluid F flows through the fluid by-pass 36 and before the second fluid passage device 34 so that the first portion F1 and the second portion F2 of the fluid F, now rejoined into rejoined fluid FR of the fluid F, flow through the second fluid passage device 34.

Figure 4:
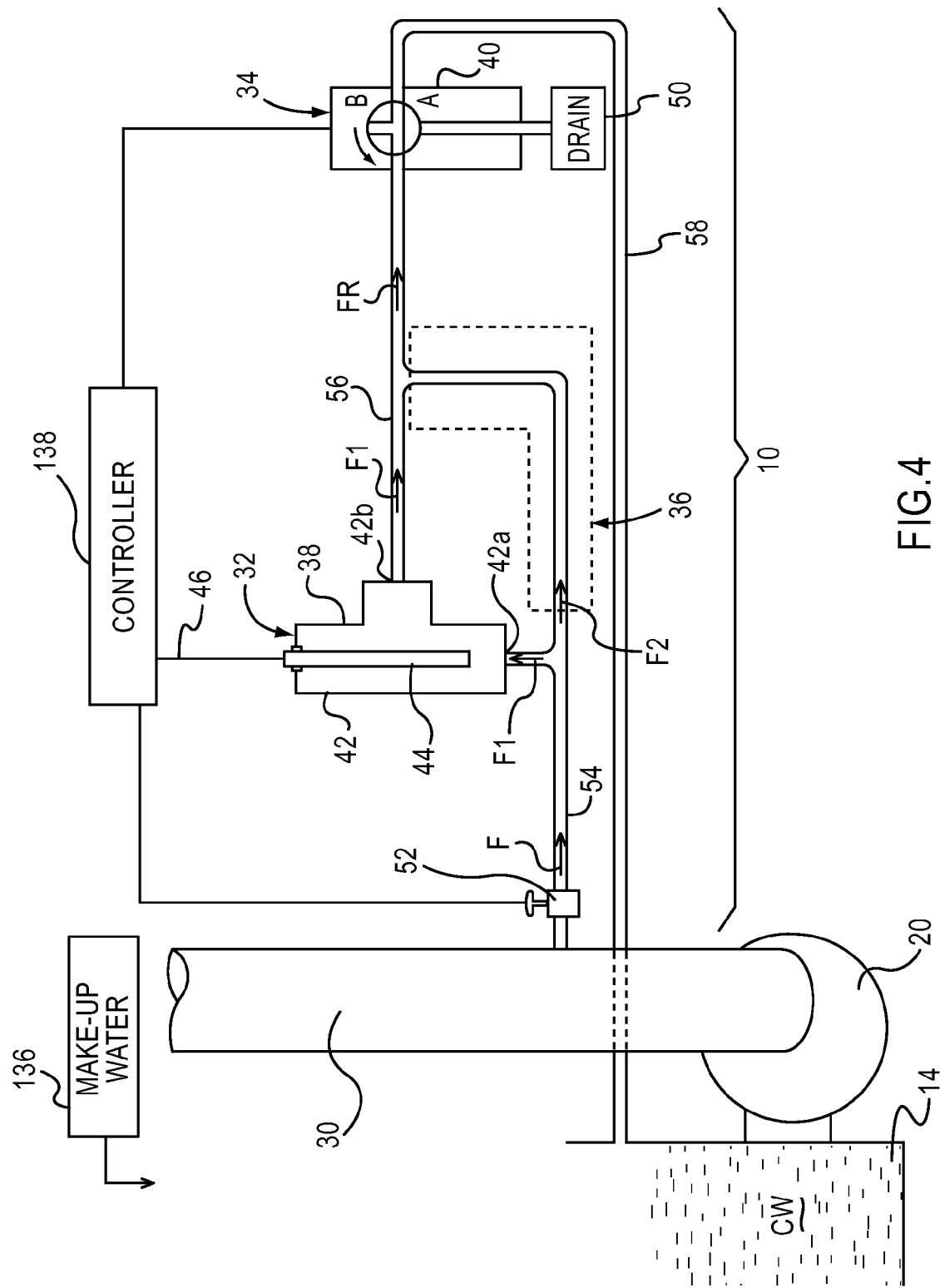
FIG. 4 is a diagrammatical view of a version of the sampling apparatus of the present invention.
Figure 5:
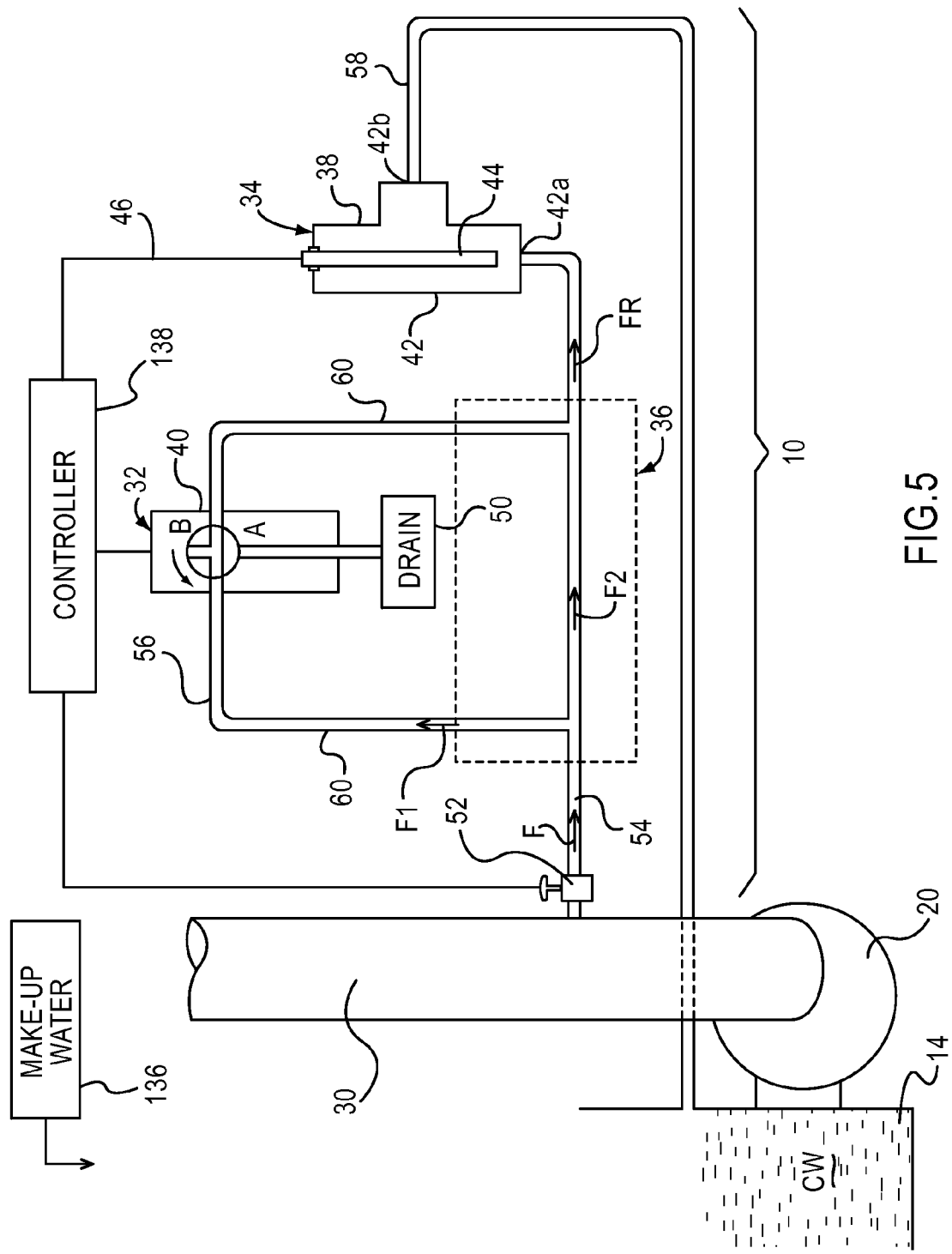
FIG. 5 is a diagrammatical view of another version of the sampling apparatus of the present invention.

With reference to FIG. 4, the first fluid passage device 32 is a sensor assembly 38 and the second fluid passage device 34 is a three-way valve assembly 40. Preferably, the three-way valve assembly 40 is a ball valve. With reference to FIG. 5, note that the first fluid passage device 32 can be the three-way valve assembly 40 and the second fluid passage device 34 can be the sensor assembly 38. In either FIG. 4 or 5, the sensor assembly 38 includes a container 42 and a sensor 44. The container 42 has a container inlet 42a and a container outlet 42b. In FIG. 4, the sensor 44 is disposed in the container 42 in a sealed manner so that the first portion F1 of the fluid F enters the container inlet 42a contacts the sensor 44 before the fluid portion F1 exits the container outlet 42b. The container inlet 42a or outlet 42b, if desired, could be sized in a manner to limit the amount of flow of the first portion F1 of the fluid F through the container 42. Thus, flow can be controlled through the container 42, if desired. In FIG. 5, note that the rejoined fluid FR enters the container inlet 42a and contacts the sensor 44 before the rejoined fluid FR exits the container outlet 42b.

The sensor 44 is operative to sense at least one characteristic of the first portion F1 of the fluid F in the container 42. The sensor 44 is operative to transmit at least one signal representative of the sensed characteristic of the first portion F1 of the fluid F that is in contact with the sensor 44 in the container 42, as is known in the art. The at least one signal is transmitted from the sensor 44 exteriorly of the container 42 via a wire 46. By way of example only and not by way of limitation, the sensor 44 is a conductivity probe and, preferably, an electrode-less conductivity probe. As is known in the art, a conductivity probe generates signals representative of a conductivity of the first portion F1 of the fluid F in contact with the conductivity probe.

Furthermore, with reference to FIG. 3, the second fluid passage device includes a second fluid passage device outlet 58 so that, as would be appreciated by one of ordinary skill in the art, the fluid F, the first and second portions F1 and F2 of the fluid F and the rejoined fluid FR can flow through the sampling apparatus 10. However, the first fluid passage device 32 might also include a first fluid passage device outlet 48.

One version of the sampling apparatus 10 illustrated in FIG. 4 will now be discussed. The sampling apparatus 10 samples conductivity of the cooling water CW in the evaporative cooler 12 via the riser pipe 30 as discussed above. The first fluid passage device 32 is the sensor assembly 38 in which the sensor 44 is a conductivity probe, hereinafter referred to as a conductivity sensor assembly, and the second fluid passage device 34 is the three-way valve assembly 40 that is disposed downstream of and is in fluid communication with the conductivity sensor assembly 38. The fluid by-pass 36 is disposed downstream of the riser pipe 30 and upstream of the three-way valve assembly 40. The fluid by-pass 36 is in fluid communication with and disposed between the riser pipe 30 and the three-way valve assembly 40. The fluid by-pass 36 is operative to cause the first portion F1 of the cooling water CW from the riser pipe 30 to flow through the conductivity sensor assembly 38 and is operative to cause the second portion F2 of the cooling water CW to by-pass the conductivity sensor assembly 38 so that the second portion F2 of the cooling water CW flows from the riser pipe 30 to the three-way valve assembly 40 without flowing through the conductivity sensor assembly 38.

Figure 6A:
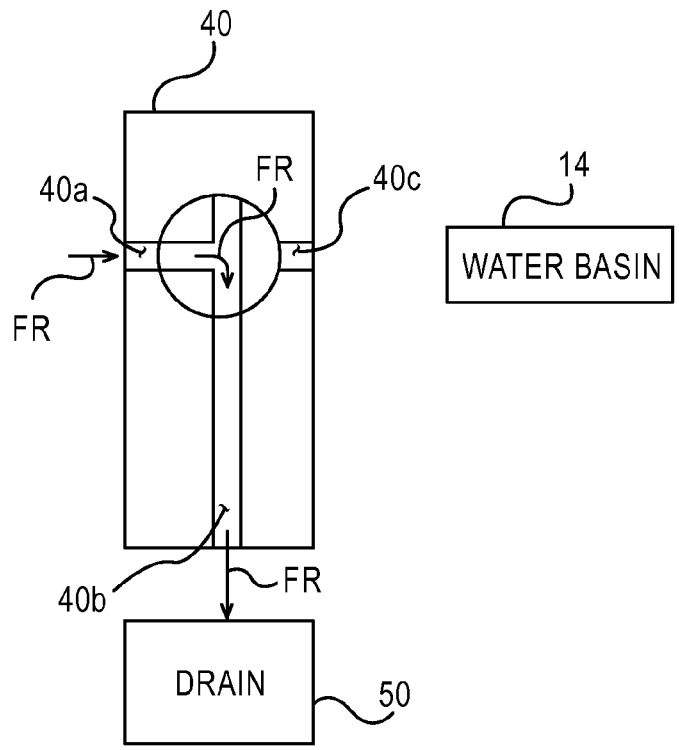
FIG. 6A is a diagrammatical view of a three-way valve assembly shown in a first fluid flow-through position
Figure 6B:
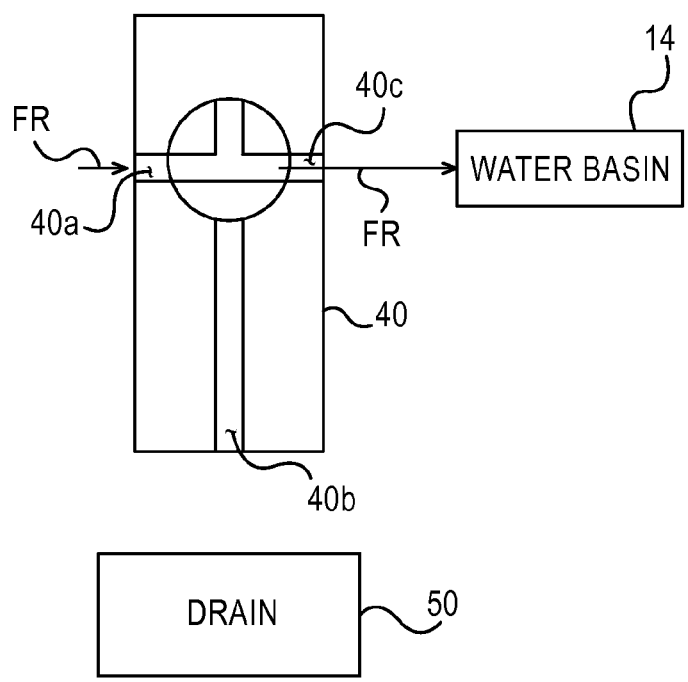
FIG. 6B is a diagrammatical view of the three-way valve assembly shown in a second fluid flow-through position

As shown in FIGS. 6A and 6B, the three-way valve assembly 40 includes a three-way valve inlet 40a, a first three-way valve outlet 40b and a second three-way valve outlet 40c. The three-way valve assembly 40 is operative to move to and between a first flow-through position as shown in FIG. 6A and a second flow-through position as shown in FIG. 6B. In the first flow-through position (FIG. 6A), the rejoined cooling water FR, i.e. the first portion F1 of the cooling water CW and the second portion F2 of the cooling water CW rejoined, flow into the three-way valve inlet 40a and discharges from the first three-way valve outlet 40b and into a drain 50. In the second flow-through position (FIG. 6B), the rejoined first and second portions FR of the cooling water CW flow into the three-way valve inlet 40a and discharge from the second three-way valve outlet 40c and back into the water basin 14 as illustrated in FIG. 4 and represented in FIG. 6B. However, one of ordinary skill in the art would appreciate that the three-way valve assembly 40 can be re-arranged so that, in the first flow-through position, the rejoined cooling water FR can discharge to the water basin 14 and, correspondingly, in the second flow-through position, the rejoined cooling water FR can discharge to the drain 50.

Further, with reference to FIG. 4, the second fluid passage device 34 is the three-way valve assembly 40 shown in FIGS. 6A and 6B. As shown in FIG. 4, with the three-way valve assembly in the second flow-through position, the rejoined fluid FR discharges to the water basin 14. However, one of ordinary skill in the art would appreciate that the three-way valve assembly could be re-arranged so that rejoined fluid FR discharges to the drain when the three-way valve assembly is in the second flow-through position.

Figure 7A:
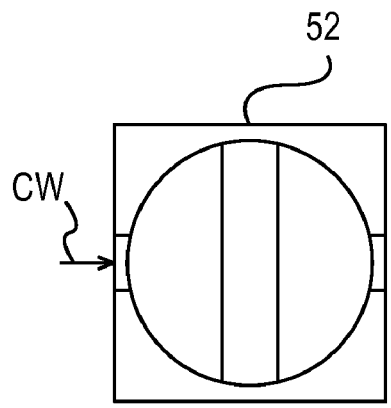
FIG. 7A is a diagrammatical view of an isolation and flow control valve in a fully-closed state.
Figure 7B:
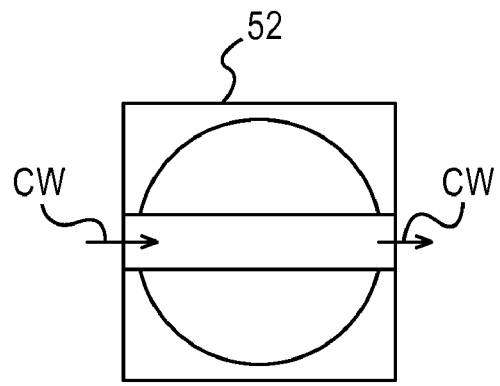
FIG. 7B is a diagrammatical view of the isolation and flow control valve in a wide-opened state.
Figure 7C:
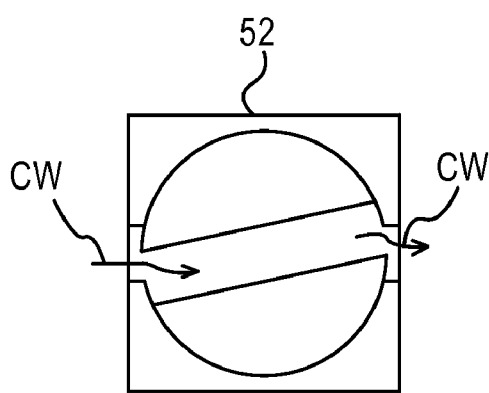
FIG. 7C is a diagrammatical view of the isolation and flow control valve in a partially-opened state.

In FIGS. 4 and 7A-7C, the sampling apparatus 10 also includes an isolation and flow control valve 52. The particular valve shown is a ball valve, but as would be appreciated by one of ordinary skill in the art, any of the various types of valves could be used. The isolation and flow control valve 52 is disposed between the riser pipe 30 and the fluid by-pass 36 and is operative to move to and between a fully-closed state (FIG. 7A) and a wide-opened state (FIG. 7B) and a partially-opened state (FIG. 7C) which is between the fully-closed state and the wide-opened state. When the isolation and flow control valve 52 is disposed in the fully-closed state (FIG. 7A), the cooling water CW is prevented from flowing from the riser pipe 30 and into the conductivity sensor assembly 38, the three-way valve assembly 40 and the fluid by-pass 36. In the wide-opened state (FIG. 7B), a maximum amount of the cooling water CW is permitted to flow from the riser pipe 30 and into the conductivity sensor assembly 38, the three-way valve assembly 40 and the fluid by-pass 36. In the partially-opened state (FIG. 7C), a controlled amount of the cooling water CW, being less than the maximum amount of cooling water CW illustrated in FIG. 7B, is permitted to flow from the riser pipe 30 and into the conductivity sensor assembly 38, the three-way valve assembly 40 and the fluid by-pass 36.

Again, with reference to FIG. 4, the sampling apparatus 10 includes a first horizontally-extending conduit 54 and a second horizontally-extending conduit 56 that extends parallel to and is disposed above the first horizontally-extending conduit 54. Note that the conductivity sensor assembly 38 is disposed between and interconnects the first and second horizontally-extending conduits 54 and 56 respectively. The three-way valve assembly 40 is connected to the second horizontally-extending conduit 56. The first horizontally-extending conduit 54 is connected to the riser pipe 30 above the pump 20 and, preferably, above the water basin 14. With this horizontal-conduit arrangement, when the pump 20 is deactivated and the isolation and flow control valve 52 is either in a wide-opened state (FIG. 7b) or a partially-opened state (FIG. 7c), the cooling water CW contained in the sampling apparatus can drain from the sampling apparatus 10. In the pump-deactivated condition, some of the cooling water CW in the sampling apparatus 10 will drain back into the riser pipe 30 and subsequently into the water basin 14 as a result of gravity and some of the cooling water CW will drain downstream of the three-way valve assembly 40 directly into the water basin 14 as a result of gravity. The three-way valve itself will also drain as a result of gravity regardless of its position as shown in FIGS. 6A and 6B. As a result, during winter operations of the conventional evaporative cooler 12, there is no need to heat and/or insulate the sampling apparatus 10 to prevent freezing of the sampling apparatus 10.

The sampling apparatus 10 is operative in conjunction with the controller 138 and make-up water source 136 as in the prior art. No further description is therefore deemed necessary.

Another version of the sampling apparatus 10 of the present invention is illustrated in FIG. 5. This version is similar to the one describe above except that the first fluid passage device 32 is the three-way valve assembly 40 and the second fluid passage device 34 is the conductivity sensor assembly 38. Note that the sampling apparatus includes the first horizontally-extending conduit 54, the second horizontally-extending conduit 56 as well as a third horizontally-extending conduit 58 and a pair of disposed-apart vertically-extending conduits 60 that interconnect the first horizontally-extending conduit 54 and the second horizontally-extending conduit 56. The second horizontally-extending conduit 56 and the third horizontally-extending conduit 58 extend parallel to and above the first horizontally-extending conduit 54. The three-way valve assembly 40 is disposed on the second horizontally-extending conduit 56 above the first horizontally-extending conduit 54 and between the pair of disposed-apart vertically-extending conduits 60. The conductivity sensor assembly 38 is connected to and disposed between the first horizontally-extending conduit 54 and third horizontally-extending conduit 58 and is disposed above the first horizontally-extending conduit 54. Further, the first horizontally-extending conduit 54 is connected to the riser pipe 30 above the pump 20 and, preferably, above the water basin 14. In addition, the third horizontally-extending conduit 58 is in fluid communication with the water basin 14.

With this horizontal-conduit arrangement, when the pump 20 is deactivated and the isolation and flow control valve 52 is either in a wide-opened state (FIG. 7b) or a partially-opened state (FIG. 7c), the cooling water CW contained in the sampling apparatus can drain from the sampling apparatus 10. In the pump-deactivated condition, some of the cooling water CW in the sampling apparatus 10 will drain back into the riser pipe 30 and subsequently into the water basin 14 as a result of gravity and some of the cooling water CW will drain downstream of the conductivity sensor assembly 38 directly into the water basin 14 as a result of gravity. The three-way valve itself will also drain as a result of gravity regardless of its position as shown in FIGS. 6A and 6B. As a result, during winter operations of the conventional evaporative cooler 12, there is no need to heat and/or insulate the sampling apparatus 10 to prevent freezing of the sampling apparatus 10.

Also, the container inlet 42a or outlet 42b, if desired, could be sized in a manner to limit the amount of flow of the rejoined fluid FR of the fluid F through the container 42. Thus, flow can be controlled through the container 42, if desired.

This version of the sampling apparatus 10 of the present invention is operative in conjunction with the controller 138 and make-up water source 136 as in the prior art. No further description is therefore deemed necessary.

Typically, a conductivity probe requires a minimum amount of fluid to flow thereacross for proper operation while simultaneously limits the amount of flow to a maximum flow rate thereacross. Exceeding the maximum flow rate can damage the conductivity probe. Since the container inlet 42a or outlet 42b can be sized in a manner to assure that the maximum flow rate of the fluid across the conductivity probe cannot be exceed, the sampling apparatus 10 of the present invention is not sensitive to the flow rate of the mineral-laden re-circulating cooling water during blow-down even though the sensor assembly 38 and three-way valve assembly 40 are in fluid communication with each other in a common fluid circuit.

The present invention, may, however, be embodied in various different forms and should not be construed as limited to the exemplary embodiments set forth herein; rather, this exemplary embodiment and the described versions of the same are provided so that this disclosure will be thorough and complete and will fully convey the scope of the present invention to those skilled in the art.

What is claimed is:

1. A sampling apparatus for sampling a fluid from a fluid source, comprising:
    a first fluid passage device disposed downstream of and in fluid communication with the fluid source;
    a second fluid passage device disposed downstream of and in fluid communication with the first fluid passage device; and
    a fluid by-pass disposed downstream of the fluid source and upstream of the second fluid passage device, the fluid by-pass being in fluid communication with and between the fluid source and the second fluid passage device and operative to cause a first portion of the fluid from the fluid source to flow through the first fluid passage device and to cause a second portion of the fluid to by-pass the first fluid passage device so that the second portion of the fluid flows from the fluid source to the second fluid passage device without flowing through the first fluid passage device,
    wherein the first portion of the fluid and the second portion of the fluid rejoin each other after the first portion of the fluid flows through the first fluid passage device and the second portion of the fluid flows through the fluid by-pass and before the second fluid passage device so that the rejoined first and second portions of the fluid flow through the second fluid passage device and
    wherein the first fluid passage device is one of a sensor assembly and a three-way valve assembly and the second fluid passage device is a remaining one of the sensor assembly and the three-way valve assembly.

2. A sampling apparatus according to claim 1, wherein the sensor assembly includes a container having a container inlet and a container outlet and a sensor disposed in the container in a sealed manner such that the first portion of the fluid entering the container inlet contacts the sensor before exiting the container outlet.

3. A sampling apparatus according to claim 2, wherein the sensor is operative to sense at least one characteristic of the first portion of the fluid in the container and to transmit at least one signal representative of the sensed characteristic of the first portion of the fluid in contact with the sensor in the container, the at least one signal transmitted exteriorly of the container.

4. A sampling apparatus according to claim 1, wherein the sensor is a conductivity probe operative to generate signals representative of a conductivity of the first portion of the fluid in contact with the conductivity probe.

5. A sampling apparatus according to claim 1, wherein at least one of the first fluid passage device and the second fluid passage device includes an outlet.

6. A sampling apparatus for sampling conductivity of cooling water in an evaporative cooling system having a water basin, a cooling water distribution system positioned above the water basin, a pump in fluid communication with the water basin for pumping the cooling water from the water basin to the cooling water distribution system, a riser pipe disposed between and interconnecting the pump and the cooling water distribution system, the sampling apparatus comprising:
    a conductivity sensor assembly disposed downstream of and in fluid communication with the riser pipe;
    a three-way valve assembly disposed downstream of and in fluid communication with the conductivity sensor assembly; and
    a fluid by-pass disposed downstream of the riser pipe and upstream of the three-way valve assembly, the fluid by-pass being in fluid communication with and between the riser pipe and the three-way valve assembly and operative to cause a first portion of the cooling water from the riser pipe to flow through the conductivity sensor assembly and to cause a second portion of the cooling water to by-pass the conductivity sensor assembly so that the second portion of the cooling water flows from the riser pipe to the three-way valve assembly without flowing through the conductivity sensor assembly.

7. A sampling apparatus according to claim 6, wherein the first portion of the cooling water and the second portion of the cooling water rejoin each other after the first portion of the cooling water flows through the conductivity sensor assembly and the second portion of the cooling water flows through the fluid by-pass and before the three-way valve assembly so that the rejoined first and second portions of the cooling water flow through the three-way valve assembly.

8. A sampling apparatus according to claim 6, wherein the conductivity sensor assembly includes a container having a container inlet and a container outlet and a conductivity sensor disposed in the container in a sealed manner such that the first portion of the cooling water entering the container inlet contacts the conductivity sensor before exiting the container outlet.

9. A sampling apparatus according to claim 8, wherein the conductivity sensor is operative to sense conductivity of the first portion of the cooling water in the container and to transmit at least one signal representative of the conductivity of the first portion of the cooling water in contact with the conductivity sensor in the container, the at least one signal transmitted exteriorly of the container.

10. A sampling apparatus according to claim 6, wherein the three-way valve assembly includes a three-way valve inlet, a first three-way valve outlet and a second three-way valve outlet, the three-way valve assembly operative to move to and between a first flow-through position and a second flow-through position, in the first flow-through position, the rejoined first and second portions of the cooling water flow into the three-way inlet valve and discharges from the first three-way valve outlet and into one of a drain and the water basin and, in the second flow-through position, the rejoined first and second portions of the cooling water flow into the three-way inlet valve and discharges from the second three-way valve outlet and into a remaining one of the drain and the water basin.

11. A sampling apparatus according to claim 6, further comprising an isolation and flow control valve disposed between the riser pipe and the fluid by-pass, the isolation and flow control valve operative to move to and between a fully-closed state and a wide-opened state and a partially-opened state being between the fully-closed state and the wide-opened state.

12. A sampling apparatus according to claim 11, wherein, when the isolation and flow control valve is disposed in the fully-closed state, the cooling water is prevented from flowing from the riser pipe and into the conductivity sensor assembly, the three-way valve assembly and the fluid by-pass, in the wide-opened state, a maximum amount of the cooling water is permitted to flow from the riser pipe and into the conductivity sensor assembly, the three-way valve assembly and the fluid by-pass, and, in the partially-opened state, a controlled amount of the cooling water being less than the maximum amount of cooling water is permitted to flow from the riser pipe and into the conductivity sensor assembly, the three-way valve assembly and the fluid by-pass.

13. A sampling apparatus according to claim 11, further comprising a first horizontally-extending conduit and a second horizontally-extending conduit extending parallel to and above the first horizontally-extending conduit, the conductivity sensor assembly disposed between and interconnecting the first and second horizontally-extending conduits, the three-way valve assembly connected to the second horizontally-extending conduit, the first horizontally-extending conduit connected to the riser pipe above the pump and water basin.

14. A sampling apparatus for sampling conductivity of cooling water in an evaporative cooling system having a water basin, a cooling water distribution system positioned above the water basin, a pump in fluid communication with the water basin for pumping the cooling water from the water basin to the cooling water distribution system, a riser pipe disposed between and interconnecting the pump and the cooling water distribution system, the sampling apparatus comprising:
 a three-way valve assembly disposed downstream of and in fluid communication with the riser pipe;
 a conductivity sensor assembly disposed downstream of and in fluid communication with the three-way valve assembly; and
 a fluid by-pass disposed downstream of the riser pipe and upstream of the conductivity sensor assembly, the fluid by-pass being in fluid communication with and between the riser pipe and the conductivity sensor assembly and operative to cause a first portion of the cooling water from the riser pipe to flow to the three-way valve assembly and to cause a second portion of the cooling water to by-pass the three-way valve assembly so that the second portion of the cooling water flows from the riser pipe to the conductivity sensor assembly without flowing through the three-way valve assembly.

15. A sampling apparatus according to claim 14 wherein the three-way valve assembly includes a three-way valve inlet, a first three-way valve outlet and a second three-way valve outlet, the three-way valve assembly operative to move to and between a first flow-through position and a second flow-through position, in the first flow-through position, the first portion of the cooling water flows into the three-way inlet valve and discharges from the first three-way valve outlet and to one of a drain and the conductivity sensor assembly and, in the second flow-through position, the first portion of the cooling water flows into the three-way valve inlet and discharges from the second three-way valve outlet to a remaining one of the drain and the conductivity sensor assembly.

16. A sampling apparatus according to claim 14, wherein the conductivity sensor assembly includes a container having a container inlet and a container outlet and a conductivity sensor disposed in the container in a sealed manner such that the first portion of the cooling water entering the container inlet contacts the conductivity sensor before exiting the container outlet.

17. A sampling apparatus according to claim 16, wherein the conductivity sensor is operative to sense conductivity of the first portion of the cooling water in the container and to transmit at least one signal representative of the conductivity of the first portion of the cooling water in contact with the conductivity sensor in the container, the at least one signal transmitted exteriorly of the container.

18. A sampling apparatus according to claim 14, further comprising an isolation and flow control valve disposed between the riser pipe and the fluid by-pass, the isolation and flow control valve operative to move to and between a fully-closed state and a wide-opened state and a partially-opened state being between the fully-closed state and the wide-opened state.

19. A sampling apparatus according to claim 18, wherein, when the isolation and flow control valve is disposed in the fully-closed state, the cooling water is prevented from flowing from the riser pipe and into the conductivity sensor assembly, the three-way valve assembly and the fluid by-pass, in the wide-opened state, a maximum amount of the cooling water is permitted to flow from the riser pipe and into the conductivity sensor assembly, the three-way valve assembly and the fluid by-pass, and, in the partially-opened state, a controlled amount of the cooling water being less than the maximum amount of cooling water is permitted to flow from the riser pipe and into the conductivity sensor assembly, the three-way valve assembly and the fluid by-pass.

20. A sampling apparatus according to claim 14, further comprising a first horizontally-extending conduit, a second horizontally-extending conduit, a third horizontally-extending conduit and a pair of disposed-apart vertically-extending conduits interconnecting the first horizontally-extending conduit and the second horizontally-extending conduit, the second and third horizontally-extending conduits extending parallel to and above the first horizontally-extending conduit, the three-way valve assembly disposed on the second horizontally-extending conduit above the first horizontally-extending conduit and between the pair of disposed-apart vertically-extending conduits, the conductivity sensor assembly connected to and between the first and third horizontally-extending conduits and disposed above the first horizontally-extending conduit, the first horizontally-extending conduit connected to the riser pipe above the pump and water basin, the third horizontally-extending conduit being in fluid communication with the water basin.

21. A sampling apparatus adapted for sampling a fluid from a fluid source being pumped by a pump operative to switch between a pumping state and a non-pumping state, the sampling apparatus comprising:
a first fluid passage device disposed downstream of and in fluid communication with the fluid source and the pump;
a second fluid passage device disposed downstream of and in fluid communication with the first fluid passage device;
wherein said first fluid passage device is one of a sensor assembly and a three-way valve assembly and said second fluid passage device is a remaining one of the sensor assembly and the three-way valve assembly and
wherein, when the pump is in the pumping state, the fluid flows sequentially from the fluid source, through the first fluid passage device and through the second fluid passage device and thereafter either returns to the fluid source or drains from one of the first fluid passage device and the second fluid passage device and away from the fluid source and, when the pump is in the non-pumping state, the fluid in the sampling apparatus drains therefrom by at least one of the fluid returning to the fluid source and draining away from the fluid source thereby rendering the sampling apparatus at least substantially empty of the fluid.

22. A sampling apparatus according to claim 21, further comprising a fluid by-pass disposed downstream of the fluid source and upstream of the second fluid passage device, the fluid by-pass being in fluid communication with and between the fluid source and the second fluid passage device and operative to cause a first portion of the fluid from the fluid source to flow through the first fluid passage device and to cause a second portion of the fluid to by-pass the first fluid passage device so that the second portion of the fluid flows from the fluid source to the second fluid passage device without flowing through the first fluid passage device.

23. A sampling apparatus according to claim 22, wherein the sensor assembly includes a container having a container inlet and a container outlet and a sensor disposed in the container in a sealed manner such that the first portion of the fluid entering the container inlet contacts the sensor before exiting the container outlet.

24. A sampling apparatus according to claim 23, wherein the sensor is operative to sense at least one characteristic of the first portion of the fluid in the container and to transmit at least one signal representative of the sensed characteristic of the first portion of the fluid in contact with the sensor in the container, the at least one signal transmitted exteriorly of the container.

25. A sampling apparatus according to claim 23, wherein the sensor is a conductivity probe operative to generate signals representative of a conductivity of the first portion of the fluid in contact with the conductivity probe.

26. A sampling apparatus according to claim 21, wherein at least one of the first fluid passage device and the second fluid passage device includes an outlet.

27. A sampling apparatus according to claim 21, wherein, when the pump is in the non-pumping state, the fluid in sampling apparatus drains therefrom by Earth's gravity.

* * * * *